United States Patent
Misawa et al.

(10) Patent No.: US 12,188,928 B2
(45) Date of Patent: Jan. 7, 2025

(54) COMPETITIVE IMMUNOCHROMATOGRAPHIC ANALYSIS METHOD AND IMMUNOCHROMATOGRAPHIC SENSOR

(71) Applicants: TECHNO MEDICA CO., LTD., Yokohama (JP); KEIO UNIVERSITY, Tokyo (JP)

(72) Inventors: Kazushi Misawa, Kawasaki (JP); Daniel Citterio, Kawasaki (JP); Hiroki Yamazaki, Yokohama (JP); Tomohiro Yamamoto, Yokohama (JP)

(73) Assignees: Techno Medica Co., Ltd., Kanagawa (JP); Keio University, Tokyo (JP)

( * ) Notice: Subject to any disclaimer, the term of this patent is extended or adjusted under 35 U.S.C. 154(b) by 944 days.

(21) Appl. No.: 17/055,672

(22) PCT Filed: May 16, 2019

(86) PCT No.: PCT/JP2019/019587
§ 371 (c)(1),
(2) Date: Nov. 16, 2020

(87) PCT Pub. No.: WO2019/221250
PCT Pub. Date: Nov. 21, 2019

(65) Prior Publication Data
US 2021/0199649 A1  Jul. 1, 2021

(30) Foreign Application Priority Data
May 17, 2018   (JP) .................................. 2018-095639

(51) Int. Cl.
*G01N 33/543*  (2006.01)
(52) U.S. Cl.
CPC .............................. *G01N 33/54306* (2013.01)

(58) Field of Classification Search
None
See application file for complete search history.

(56) References Cited

U.S. PATENT DOCUMENTS

| 5,120,643 A | 6/1992 | Ching et al. |
| 5,401,667 A | 3/1995 | Koike |

(Continued)

FOREIGN PATENT DOCUMENTS

| GB | 2241329 A | 8/1991 |
| JP | S64-32169 A | 2/1989 |

(Continued)

OTHER PUBLICATIONS

Misawa, K., et al. "Text-Displaying Competitive Lateral Flow Immunoassay Enabling Naked-Eye Semiquantitative Analysis," The 99th Spring annual meeting of The Chemical Society of Japan, Mar. 1, 2019, 3E1-32).

(Continued)

*Primary Examiner* — Juliet C Switzer
*Assistant Examiner* — Alexander Alexandrovic Volkov
(74) *Attorney, Agent, or Firm* — Stites & Harbison, PLLC; Jeffrey A. Haeberlin; Patrick M. Torre

(57) ABSTRACT

[Problem to be solved by the invention]
The purpose of the present invention is to provide a competitive immunochromatographic analysis method and immunochromatographic sensor using said analysis method capable of intuitively displaying a molecular concentration of a substance to be measured and facilitating visual judgement of the molecular concentration.
[Problem to be solved by the invention]
Competitive immunochromatographic analysis method according to the present invention is characterized in that the method comprises
a step for supplying a mixed solution, in which a test solution containing a substance to be measured A and (Continued)

a labeled antibody B are mixed, to one or more judgement parts wherein said judgement parts are formed by immobilizing a text antibody C which specifically reacts with the labeled antibody B specifically reacting with the substance to be measured A on a membrane carrier in the form of character(s) or figure(s) and immobilizing a mask antigen D composed of the same antigen as the substance to be measured A on the membrane carrier so as to surround said text antibody C, a step for competitively binding the labeled antibody B to the substance to be measured A, the mask antigen D and the text antibody C on the judgement parts, a step for judging the concentration of the substance to be measured A based on the signal from the labeled antibody B bound to the text antibody C and the mask antigen D.

8 Claims, 11 Drawing Sheets

(56) References Cited

U.S. PATENT DOCUMENTS

| | | | | |
|---|---|---|---|---|
| 5,565,326 A | * | 10/1996 | Daiss | G01N 33/54306 436/523 |
| 5,578,577 A | | 11/1996 | Ching et al. | |
| 5,916,757 A | * | 6/1999 | Contestable | G01N 33/581 436/523 |
| 2001/0006821 A1 | | 7/2001 | Ching et al. | |
| 2007/0264664 A1 | * | 11/2007 | Akhavan-Tafti | G01N 33/54306 435/7.93 |

FOREIGN PATENT DOCUMENTS

| | | |
|---|---|---|
| JP | H04-279860 A | 10/1992 |
| JP | H04-299262 A | 10/1992 |
| JP | 2001-013143 A | 1/2001 |
| JP | 2002-340890 A | 11/2002 |
| JP | 2007-218593 A | 8/2007 |
| JP | 2008032494 A * | 2/2008 |
| JP | 2017134027 A * | 8/2017 |

OTHER PUBLICATIONS

Japan Patent Office, International Search Report issued in corresponding Application No. PCT/JP2019/019587, mailed Aug. 20, 2019.

Japan Patent Office, Written Opinion of the International Searching Authority issued in corresponding Application No. PCT/JP2019/019587, mailed Aug. 20, 2019.

* cited by examiner (a) (b)

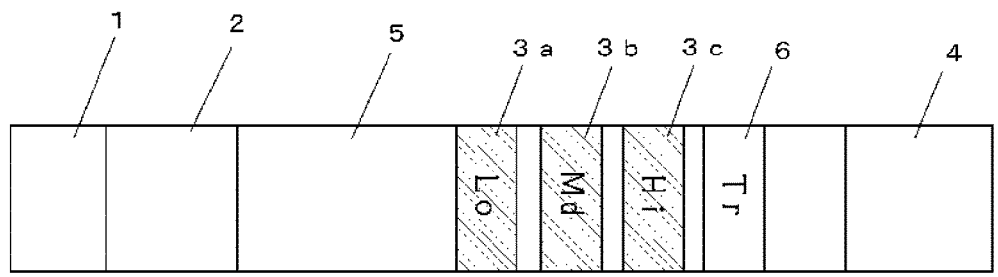
FIG.14
FIG.15
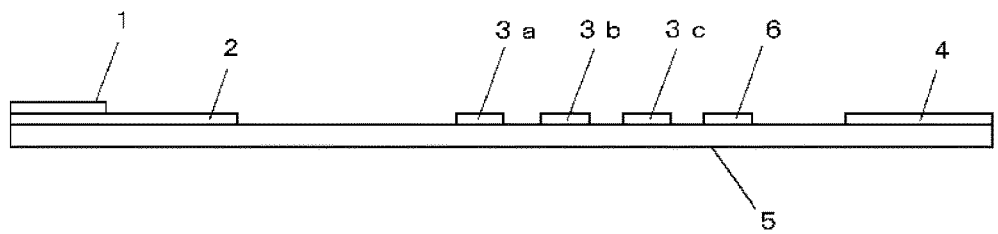
FIG.16

COMPETITIVE IMMUNOCHROMATOGRAPHIC ANALYSIS METHOD AND IMMUNOCHROMATOGRAPHIC SENSOR

TECHNICAL FIELD

The present invention relates to a competitive immunochromatographic analysis method capable of semi-quantitatively visually observing the molecular concentration of a measurement target substance in a test solution, and an improved immunochromatographic sensor using said analysis method.

STATE OF THE ART

Recently, as clinical examinations have diversified, more and more attention is drawn on performing real-time examinations, so-called POCT (Point of care testing), at clinical sites. A sensor using competitive immunochromatography method has already been proposed as one of the simple inspection methods for realizing POCT (Patent Document 1). The immunochromatographic sensor described in Patent Document 1 is a sensor for measuring a biopyrin. Said sensor comprises an impregnating member impregnated with a labeled substance obtained by labeling a bound substance containing the biopyrin and a polymer compound with a labeling substance, and a membrane carrier having a capture part on which an anti-bilirubin antibody is fixed, wherein in the impregnating member the labeled substance is mixed with a test solution and then the mixed solution consisting of the labeled substance and the test solution is subjected to chromatographic development on the membrane carrier toward the capture part so that at the capture part the biopyrin in the labeled substance and in the test solution are allowed to competitively react with the anti-bilirubin antibody and the biopyrin in the labeled substance and in the test solution are allowed to be competitively captured on the capture part.

With the above configuration of the sensor, if the biopyrin is not present in the test solution, only the labeled substance is captured by the antibody-antigen reaction with the anti-bilirubin antibody fixed on the capture part so that the capture part is strongly colored.

On the other hand, if the biopyrin is present in the test solution, not only the labeled substance but also biopyrin in the test solution is competitively captured at the capture part so that the coloration at the capture part is to be weak.

According to the above-mentioned principle, it is possible to visually judge the presence or absence of biopyrin in the test solution based on the color of the capture site in said conventional sensor.

PRIOR ART DOCUMENTS

Patent Document

[Patent document 1] Japanese patent Kokai No. 2007-218593

SUMMARY OF THE INVENTION

Problem to be Solved by the Invention

According to the said conventional competitive immunochromatographic sensor, the result can be visually judged simply by adding the test solution onto the sensor, and thus it is useful as a sensor for an immediate inspection.

However, in said conventional competitive immunochromatographic sensor, the result signal (i.e. color) of the test line (i.e. capture part) shows a negative correlation with the molecular concentration of the substance to be measured in the test solution so that there is a problem that the result signal (i.e. color) to be displayed is not intuitive and therefore, a user may erroneously judge the result. Specifically, in the sensor described in Patent Document 1, the greater the amount of biopyrin in the test solution, the lighter the color of the capture part, and conversely, the lower the amount of the biopyrin in the test solution, the darker the color of the capture part. Usually, the greater the amount of a substance in a test solution, the stronger the color of the capture part is expected. Therefore, in the above-mentioned configuration of the conventional sensor, the user may misunderstand that the amount of the biopyrin is large when the color of the capture part is dark.

In addition, according to the conventional competitive immunochromatography method, the molecular concentration of the substance to be measured must be judged based on the color density of a test line (i.e. the capture part), but it is very difficult for a human to judge the concentration based on the color density. It is also difficult to determine a cutoff value and therefore, a quantification in a narrow concentration range is impossible.

The purpose of the present invention is to provide a competitive immunochromatographic analysis method and immunochromatographic sensor using said analysis method capable of intuitively displaying a molecular concentration of a substance to be measured and facilitating visual judgement of the molecular concentration to solve the above-mentioned problems of the conventional method.

Means for Solving the Problem

In order to achieve the above objective, a competitive immunochromatographic analysis method according to the present invention is characterized in that the method comprises a step for supplying a mixed solution, in which a test solution containing a substance to be measured and a labeled antibody are mixed, to one or more judgement parts wherein said judgement parts are formed by immobilizing a text antibody which specifically reacts with the labeled antibody specifically reacting with the substance to be measured on a membrane carrier in the form of character(s) or figure(s) and immobilizing a mask antigen composed of the same antigen as the substance to be measured on the membrane carrier so as to surround said text antibody, a step for competitively binding the labeled antibody to the substance to be measured, the mask antigen and the text antibody on the judgement parts, and a step for judging the concentration of the substance to be measured based on the signal from the labeled antibody bound to the text antibody and the mask antigen.

In said analysis method, a plurality of judgement parts may be provided, and the ratios of the amounts of the text antibody and the mask antigen in each judgement part may differ from each other.

In said analysis method, a plurality of judgement parts may be provided on the membrane carrier along the flow direction of the test solution, and the ratio of the amount of mask antigen related to the text antibody on a judgement part placed downstream may be lower than the ratio of the amount of mask antigen related to the text antibody on the other judgement parts placed upstream.

Preferably, said text antibody and mask antigen may be inkjet printed on the membrane carrier.

In the case of printing, depending on the type of the text antibody and the mask antigen to be used, for example, the text antibody is first printed on the membrane carrier in the form of character(s) or figure(s), and then the mask antigen is printed so as to cover the text antibody. Alternatively, the mask antigen may be printed on the membrane carrier first, and then the text antibody may be printed on the mask antigen in the form of character(s) or figure(s). In either case, the mask antigen surrounds the text antibody.

Further, according to the present invention, a competitive immunochromatographic sensor is characterized in that the sensor comprises one or more judgement parts wherein said judgement parts are formed by immobilizing a text antibody which specifically reacts with the labeled antibody specifically reacting with the substance to be measured on a membrane carrier in the form of character(s) or figure(s) and immobilizing a mask antigen composed of the same antigen as the substance to be measured on the membrane carrier so as to surround said text antibody.

Furthermore, according to the present invention, a competitive immunochromatographic sensor is characterized in that the sensor comprises a test solution deposition section for applying a test solution containing a substance targeted for measurement, a labeled antibody containing section that is arranged downstream of the test solution deposition section and contains a labeled antibody specifically reacting with the substance targeted for measurement, at least one judgement part arranged downstream of the labeled antibody containing section, a liquid absorption part arranged downstream of the judgement part, and a membrane carrier on which the test solution deposition section, the labeled antibody containing section, the judgement part and the liquid absorption part are arranged, wherein the judgement part consists of a text antibody that specifically reacts with the labeled antibody and is immobilized on the membrane carrier in the form of character(s) or figure(s), and a mask antigen that comprises the same antigen as the substance targeted for measurement and is immobilized on the membrane carrier so as to surround the text antibody.

In said sensor, a plurality of judgement parts may be provided, wherein the ratio of the amount of the text antibody and the amount the mask antigen is different on each judgement part.

In said sensor, a plurality of judgement parts may be provided along the flow direction of the test solution wherein the ratio of the amount of mask antigen to the text antibody in the downstream judgement part is lower than the ratio of that in the upstream judgement part. Alternatively, a plurality of judgement parts may be provided along the flow direction of the test solution, wherein the ratio of the amount of mask antigen to the text antibody in the downstream judgement part is higher than the ratio of that in the upstream judgement part.

Preferably, the text antibody and the mask antigen may be printed by an inkjet printer. In this case, the amounts of the text antibody and the mask antigen may be adjusted by adjusting the number of printing cycles. In the case of printing, depending on the type of the text antibody and the mask antigen to be used, for example, the text antibody is first printed on the membrane carrier in the form of character(s) or figure(s), and then the mask antigen is printed so as to cover the text antibody. Alternatively, the mask antigen may be printed on the membrane carrier first, and then the text antibody may be printed on the mask antigen in the form of character(s) or figure(s). In either case, the mask antigen surrounds the text antibody.

Effect of the Invention

The competitive immunochromatographic analysis method according to the present invention is characterized in that the method comprises a step for supplying a mixed solution, in which a test solution containing a substance to be measured and a labeled antibody are mixed, to one or more judgement parts wherein said judgement parts are formed by immobilizing a text antibody which specifically reacts with the labeled antibody specifically reacting with the substance to be measured on a membrane carrier in the form of character(s) or figure(s) and immobilizing a mask antigen composed of the same antigen as the substance to be measured on the membrane carrier so as to surround said text antibody, a step for competitively binding the labeled antibody to the substance to be measured, the mask antigen and the text antibody on the judgement parts, a step for judging the concentration of the substance to be measured based on the signal from the labeled antibody bound to the text antibody and the mask antigen.

Whereas the labeled antibody specifically reacts with the substance to be measured, the mask antigen and text antibody, the substance to be measured does not react specifically with the text antibody.

Therefore, the mixed solution of the labeled antibody and the test solution is supplied to the judgement part, the labeled antibody competitively reacts with the substance to be measured contained in the test solution, the mask antigen and the text antibody immobilized on the judgement part.

Here, the labeled antibody bound to the substance to be measured cannot bind to the mask antigen, but can bind to the text antibody. In addition, the labeled antibody that is not bound to the substance to be measured can bind to both the mask antigen and text antibody.

And on the judgement part, the text antibody is laid out so as to represent a character(s) or figure(s) and the mask antigen is laid out to surround the text antibody.

When the amount of the substance targeted for measurement contained in the test solution is small, the proportion of the labeled antibody that binds to the text antibody does not change, but the amount of the labeled antibody that binds to the substance targeted for measurement is relatively small. Therefore, the amount of the labeled antibody bound to the mask antigen is relatively large. That is, although in addition to the labeled antibody that is not bound to the substance targeted for measurement, the labeled antibody that is bound to the substance targeted for measurement binds to the text antibody, the amount of the labeled antibody to be bound to the substance targeted for measurement is relatively small and the amount of the labeled antibody to be bound to the mask antigen is relatively large. As a result, since the judgement part develops color as a whole, the character(s) or figure(s) formed by the text antibody become invisible.

When the amount of the substance targeted for measurement contained in the test solution is large, the proportion of the labeled antibody that binds to the text antibody does not change, but the amount of the labeled antibody that binds to the substance targeted for measurement is relatively large. Therefore, the amount of the labeled antibody bound to the text antigen is relatively large. In this case, since the labeled antibody that has been bound to the substance targeted for measurement cannot bind to the mask antigen, the amount of the labeled antibody to be bound to the mask antigen is relatively small. In addition to the labeled antibody that is not bound to the substance targeted for measurement, the labeled antibody that is bound to the substance targeted for measurement binds to the text antibody, and the amount of the labeled antibody to be bound to the mask antigen is relatively small. As a result, since the color development of the portion of the mask antigen in the judgement part becomes weaker than the portion of the text antibody in the judgement part, the character(s) or figure(s) formed by the text antibody become visible.

As described above, according to the competitive immunochromatographic analysis method of the present invention, the result of the analysis may be judged not by the shades of the color based on the color reaction of the judgement part but by the appearance of characters, figures or the like on the judgement part that appear due to the contrast between the color of the text antibody part and the color of the mask antigen part. Therefore, it becomes easy to judge. It is also possible to control the cutoff value by adjusting the amount of the text antibody and the mask antigen to be immobilized on the judgement part.

In the conventional analysis method, when the test line is colored, the test is judged to be negative, and when the test line is not colored, it is judged to be positive. However, in order to completely prevent the test line from coloring when the test is positive, the concentration of the substance targeted for measurement in the test solution must be high to some extent, resulting in a drawback of poor test sensitivity. According to the analysis method of the present invention, the judgement can be made based on the character(s) or figure(s) appearing due the contrast between the color of the text antibody part and the color of the mask antigen part. Therefore, even if the mask antigen part (mask part) is colored to some extent, the test can be judged to be positive by the appearance of the character(s) or figure(s) due to the coloration of the text antibody part.

Further, as described above, according to the competitive immunochromatographic analysis method of the present invention, the larger the amount of the substance targeted for measurement in the test solution, the easier it is to see the character(s) or figure(s), whereas the smaller the amount of the substance targeted for measurement in the test solution, the more difficult it is to see the character(s) or figure(s). In addition, if the substance targeted for measurement is not contained in the test solution, the character(s) or figure(s) will not be visible. Therefore, the judgement result shows a positive correlation with respect to the concentration of the substance targeted for measurement in the test solution so that the user does not misunderstand the judgement result.

Further, by providing a plurality of judgement parts and changing the ratio of the amounts of the text antibody and the mask antigen in each judgement part, it is possible to perform analysis with a plurality of judgement parts having different conditions for the same test solution. As a result, it is possible to judge more accurately. In addition, the cutoff value can be easily set by using the judgement results of a plurality of judgement parts having different conditions.

Further, by providing a plurality of judgement parts on the membrane carrier along the flow direction of the test solution, and changing the ratios of the amount of the mask antigen with respect to the amount of the text antibody between the upstream judgement part and the downstream judgement part, it becomes possible to judge by comparing the appearance of character(s) or figure(s) in the upstream judgement part with the appearance of character(s) or figure(s) in the downstream judgement part so that it is possible to judge more accurately and more easily.

Furthermore, by inkjet printing the text antibody and the mask antigen on the membrane carrier, it becomes possible to extremely easily fabricate the judgement part. Further, by using inkjet printing, it becomes possible to freely and easily select characters and figures made of the text antibody, and it also becomes possible to easily adjust the amount of the text antibody and the mask antigen. Specifically, for example, by increasing or decreasing the number of printing cycles, it is possible to increase or decrease the amount of the text antibody and the mask antigen. Therefore, by changing the number of printing cycles, it is possible to adjust the density of the text antibody and the mask antigen on the judgement part.

It is possible to easily judge the concentration of the substance targeted for measurement in the test solution by simply dropping the test solution on the judgement part since a competitive immunochromatographic sensor according to the present invention comprises one or more judgement parts wherein said judgement parts are formed by immobilizing a text antibody which specifically reacts with the labeled antibody specifically reacting with the substance to be measured on a membrane carrier in the form of character(s) or figure(s) and immobilizing a mask antigen composed of the same antigen as the substance to be measured on the membrane carrier so as to surround said text antibody.

Further, it is possible to easily judge the concentration of the substance targeted for measurement in the test solution simply by applying the test solution on the test solution deposition section since a competitive immunochromatographic sensor according to the present invention comprises a test solution deposition section for applying a test solution containing a substance targeted for measurement, a labeled antibody containing section that is arranged downstream of the test solution deposition section and contains a labeled antibody specifically reacting with the substance targeted for measurement, at least one judgement part arranged downstream of the labeled antibody containing section, a liquid absorption part arranged downstream of the judgement part, and a membrane carrier on which the test solution deposition section, the labeled antibody containing section, the judgement part and the liquid absorption part are arranged, wherein the judgement part consists of a text antibody that specifically reacts with the labeled antibody and is immobilized on the membrane carrier in the form of character(s) or figure(s), and a mask antigen that is composed of the same antigen as the substance targeted for measurement and is immobilized on the membrane carrier so as to surround the text antibody.

BRIEF DESCRIPTION OF DRAWINGS

FIG. 14 is a schematic top view of a fourth embodiment of the immunochromatographic sensor according to the present invention.

FIG. 15 is a schematic side view of the immunochromatographic sensor shown in FIG. 14.

FIG. 16 is a diagram showing the amount of the text antibody and the mask antigen on the judgement parts by the number of printing cycles.

MODE FOR CARRYING OUT THE INVENTION

Hereinafter the mode for carrying out a competitive immunochromatographic analysis method and an immunochromatographic sensor according to the present invention will be described with reference to some embodiments shown in the accompanying drawings.

At first, the competitive immunochromatography analysis method according to the present invention will be described below.

FIG. 1(a) is a conceptual diagram showing the relationship between substance targeted for measurement, mask antigen, and text antibody used in the competitive immunochromatographic analysis method according to the present invention. FIG. 1(b) is a conceptual diagram of a judgement part of the immunochromatographic sensor executing said analysis method.

Figure 1:
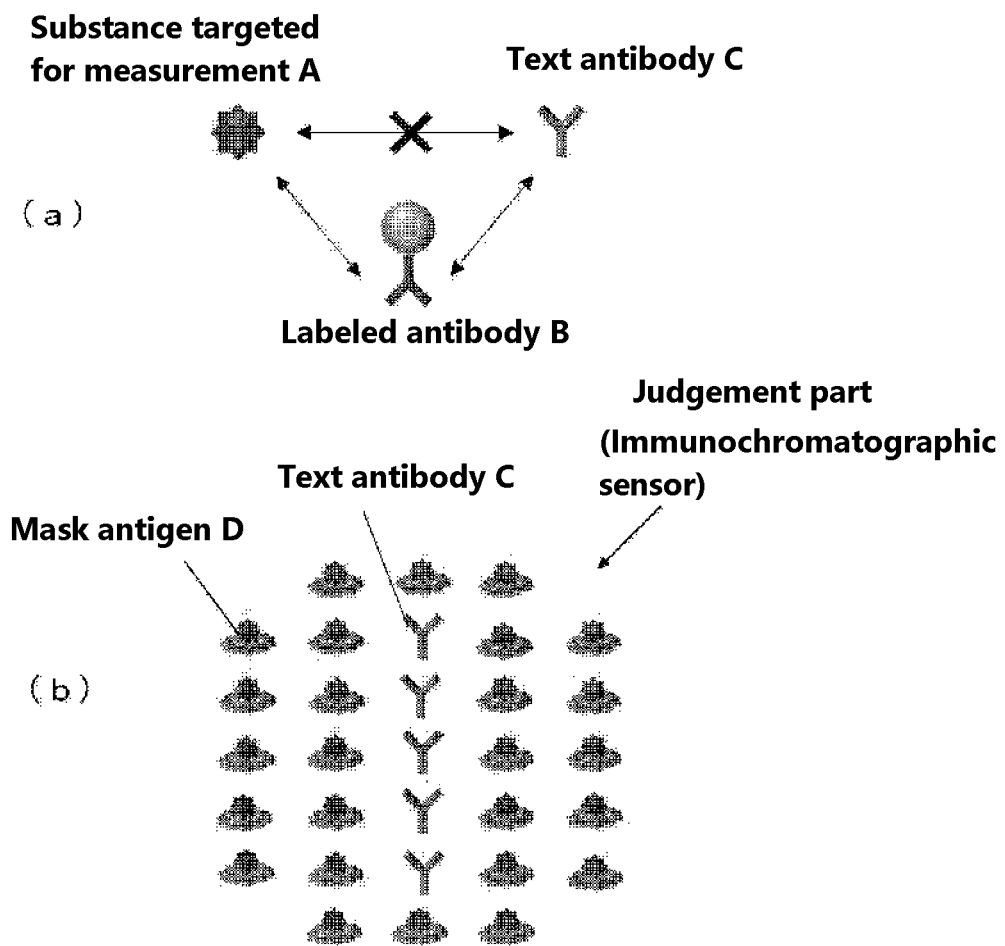
FIG. 1(a) is a conceptual diagram showing the relationship between a substance to be measured, a mask antigen, and a text antibody used in the competitive immunochromatographic analysis method according to the present invention.
FIG. 1(b) is a conceptual diagram of a judgement part of an immunochromatographic sensor executing said analysis method.

As shown in the drawings, the competitive immunochromatographic analysis method is used to semi-quantify the concentration of the substance targeted for measurement A contained in a test solution. In FIG. 1, the reference symbol B indicates a labeled antibody that specifically reacts with the substance targeted for measurement and the reference symbol C indicates an antibody that specifically reacts with the labeled antibody B (hereinafter referred to as "text antibody C" in this specification). The text antibody C does not react with the substance targeted for measurement.

As shown in FIG. 1(b), the text antibody C is immobilized on a judgement part in the form of character(s) or figure(s) (in this embodiment, the numeral "1"). In addition, an antigen D corresponding to the substance targeted for measurement A is immobilized so as to surround the text antibody C on the judgement part. Hereinafter the antigen D is referred to as "mask antigen D" in this specification.

Preferably, the text antibody C and the mask antigen D may be printed by an inkjet method. Specifically, for example, the text antibody C may be printed on a membrane carrier in an arbitrary form (the numeral "1" in this embodiment), and then the mask antigen D may be printed so as to cover the text antibody C. Alternatively, for example, the mask antigen D may be printed on the membrane carrier first, and then the text antibody C may be printed on the mask antigen D in an arbitrary form (the numeral "1" in this embodiment). Which printing method is selected may be determined depending on the type of the text antibody and the mask antigen to be used. In either method, the mask antigen D is printed to surround the text antibody C.

By using the inkjet printing to immobilize the text antibody C and the mask antigen D, it becomes easy to immobilize and arrange the text antibody C in the form of arbitrary character(s) or Figure(s). Further, since the amounts of the immobilized text antibody and the mask antigen are increased by increasing the number of printing cycles, the density of the text antibody and the mask antigen may be adjusted by adjusting the number of printing cycles.

Before judging the concentration of the substance targeted for measurement A using the judgement part described above, a mixed solution in which the labeled antibody B is mixed with a test solution is prepared in advance.

When the mixed solution is supplied to the judgement part, the labeled antibody B competitively reacts with and binds to the substance targeted for measurement A contained in the solution, and the mask antigen D and the text antibody C immobilized on the judgement part. Here, the labeled antibody B that is not bound to the substance targeted for measurement A can be bound to both the mask antigen D and the text antibody C. However, the labeled antibody B that is bound to the substance targeted for measurement A cannot bind to the mask antigen D but can bind only to the text antibody C.

The following phenomenon occurs when the above-mentioned mixed solution of the test solution and the labeled antibody B is dropped on the judgement part.

Figure 2:
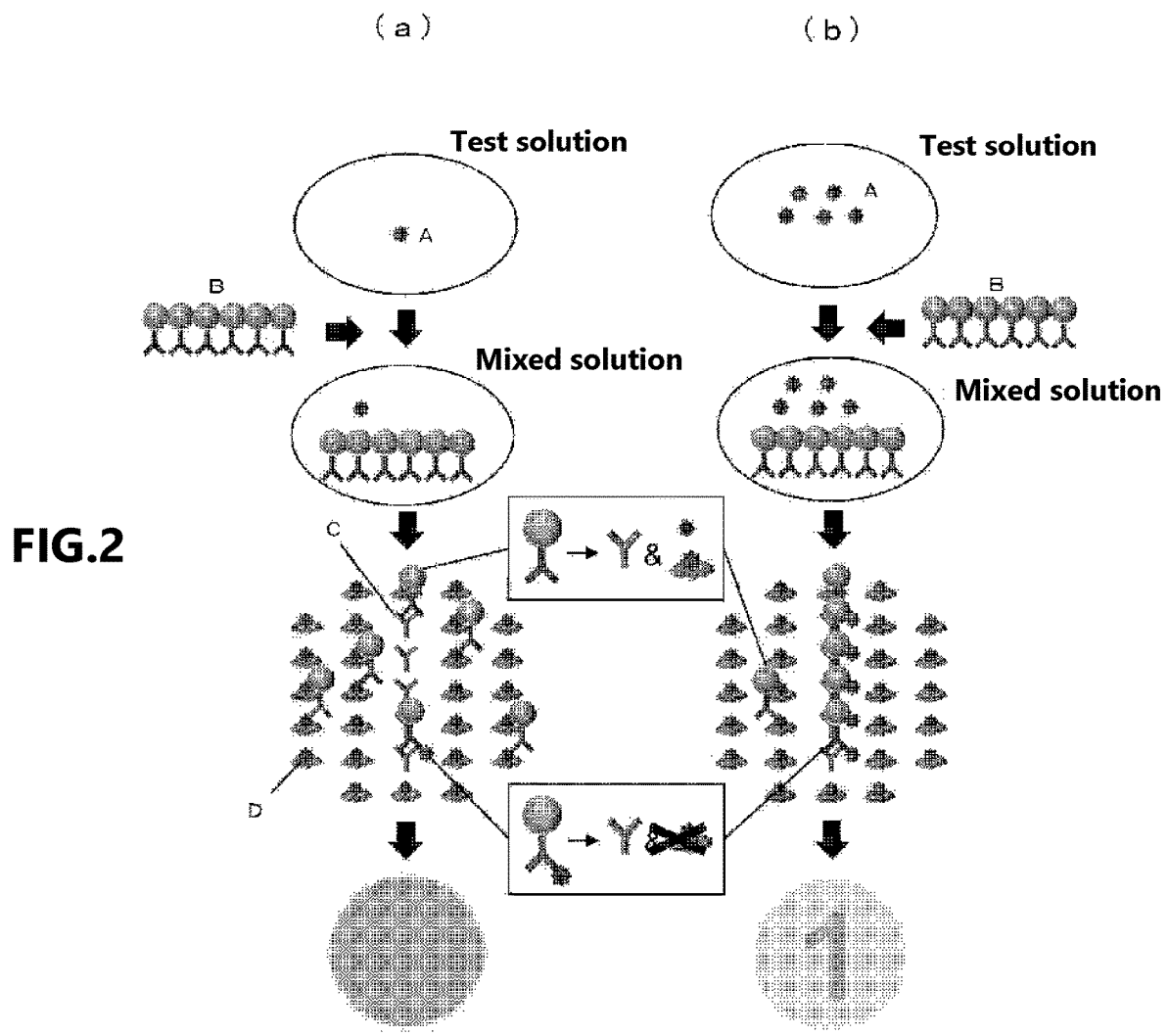
FIG. 2 is a diagram schematically showing the behavior of labeled antibody on the judgement part.

FIG. 2 is a diagram schematically showing the behavior of the labeled antibody on the judgement part.

1. In the case that the amount of the substance targeted for measurement A contained in the test solution is small:

Although the ratio of the labeled antibody B binding to the text antibody C does not change, the amount of the labeled antibody B binding to the substance targeted for measurement A becomes relatively small. As a result, the amount of labeled antibody B that is bound to the mask antigen D become relatively large. The text antibody C binds not only to the labeled antibody B that is not bound to the substance targeted for measurement A but also to the labeled antibody B bound to the substance targeted for measurement A. However, since the amount of the labeled antibody B that binds to the substance targeted for measurement A is relatively small and the amount of the labeled antibody B that binds to the mask antigen D is relatively large, the entire judgement part is colored so that the character ("1" in this embodiment) formed by the text antibody C cannot be seen from the outside (See FIG. 2(a)).

2. In the case that the amount of the substance targeted for measurement A contained in the test solution is large:

Although the ratio of the labeled antibody B binding to the text antibody C does not change, the amount of the labeled antibody B binding to the substance targeted for measurement A becomes relatively large. As a result, the amount of labeled antibody B that is bound to the text antibody C becomes relatively large. Since the labeled antibody B bound to the substance targeted for measurement A cannot bind to the mask antigen D, the amount of the labeled antibody B that is bound to the mask antigen D becomes relatively small. The text antibody C binds not only to the labeled antibody B that is not bound to the substance targeted for measurement A but also to the labeled antibody B bound to the substance targeted for measurement A. Since the amount of the labeled antibody B that binds to the mask antigen D is relatively small, the color of the area of the mask antigen B is weak and the color of the area of the text antibody C is strong, so that the character formed by the text antibody C appears on the judgement part and it can be seen (See FIG. 2(b)).

As described above, according to the competitive immunochromatographic analysis method of the present embodiment, the result of the analysis may be judged not by the shades of the color based on the color reaction of the judgement part but by the appearance of characters, figures or the like on the judgement part that appear due to the contrast between the color of the part of the text antibody C and the color of the part of the mask antigen D. Therefore, it becomes easy to judge.

Further, the larger the amount of the substance targeted for measurement A in the test solution, the easier it is to see the character(s) or figure(s), while the smaller the amount of the substance targeted for measurement A in the test solution, the harder it is to see the character(s) or figure(s). If the substance targeted for measurement A is not contained in the test solution, the character(s) or figure(s) cannot be seen. As a result, a judgement result has a positive correlation with the concentration of the substance targeted for measurement A, and the user does not misunderstand the judgement result.

Then, a second embodiment in which the judgement part configured as described above is applied to an immunochromatographic sensor having a lateral flow structure will be described.

Figure 3:
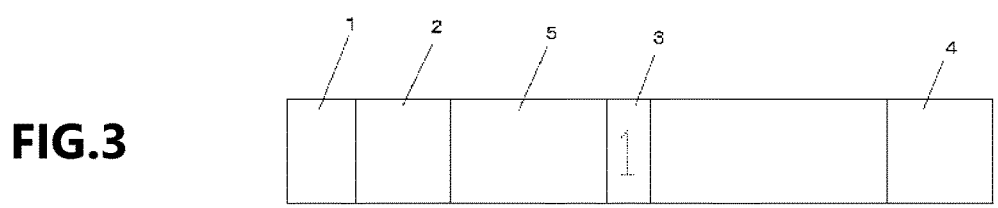
FIG. 3 is a schematic top view of a second embodiment of the immunochromatographic sensor according to the present invention.
Figure 4:
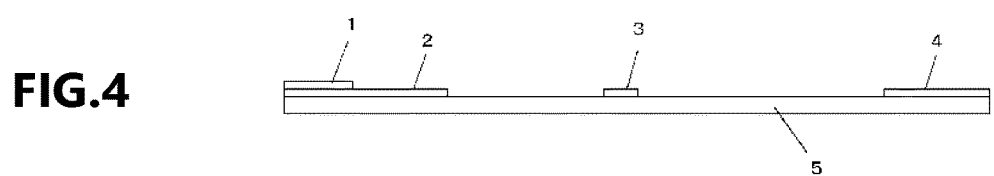
FIG. 4 is a schematic side view of the immunochromatographic sensor shown in FIG. 3.

FIG. 3 is a schematic top view of the second embodiment of the immunochromatographic sensor according to the present invention and FIG. 4 is a schematic side view of the immunochromatographic sensor shown in FIG. 3.

The multi-immunochromatographic sensor has a strip-shaped membrane carrier 5. A test solution deposition section 1 is provided at the upstream end of the membrane carrier 5 and a labeled antibody containing section 2 is provided downstream of the test solution deposition section 1. The labeled antibody containing section 2 is provided so as to partially overlap the test solution deposition section 1.

A judgement part 3 is arranged further downstream of the labeled antibody containing section 2 and a test solution absorption pad 4 is provided downstream of the judgement part 3.

The membrane carrier 5 is made of, for example, a filter paper (specifically, nitrocellulose). When the test solution is dropped onto the test solution deposition section 1, the test solution enters the labeled antibody containing section 2 due to the capillary phenomenon, and then the test solution passes through the judgement part 3 to reach the test solution absorption pad 4. Although not shown, a confirmation part in which the antibody capable of capturing a labeled antibody B is immobilized may be provided downstream of the judgement part 3. The confirmation part is used to confirm whether the test solution has normally passed through the judgement part 3.

The labeled antibody containing section 2 is impregnated with the labeled antibody B that specifically reacts with a substance targeted for measurement A. The labeled antibody B is labeled with an arbitrary labeling substance such as colloidal gold or latex.

The judgement part 3 has the same configuration as the judgement part shown in the above-described embodiment, that is, on the judgement part 3, a text antibody C that specifically reacts with the labeled antibody B is immobilized in the form of character(s) or figure(s) and a mask antigen composed of the same antigen as the substance targeted for measurement A is immobilized so as to surround the text antibody C.

According to the competitive immunochromatographic sensor configured as described above, when the test solution is dropped on the test solution deposition section 1, the test solution containing the substance targeted for measurement A enters the labeled antibody containing section 2 and is mixed with the labeled antibody B.

The mixed solution obtained by mixing the labeled antibody B and the test solution enters the judgement part 3 and in the judgement part 3, the labeled antibody B competitively reacts with the substance targeted for measurement A contained in the test solution, the mask antigen D and the text antibody C.

When the amount of the substance targeted for measurement A contained in the test solution is small, the proportion of the labeled antibody B that binds to the text antibody C does not change, but the amount of the labeled antibody B that binds to the substance targeted for measurement A is relatively small. Therefore, the amount of the labeled antibody B bound to the mask antigen D is relatively large. That is, although in addition to the labeled antibody B that is not bound to the substance targeted for measurement A, the labeled antibody B that is bound to the substance targeted for measurement A binds to the text antibody C, the amount of the labeled antibody B to be bound to the substance targeted for measurement A is relatively small and the amount of the labeled antibody B to be bound to the mask antigen D is relatively large. As a result, since the judgement part 3 develops color as a whole, the character(s) or figure(s) formed by the text antibody C become invisible.

When the amount of the substance targeted for measurement A contained in the test solution is large, the proportion of the labeled antibody B that binds to the text antibody C does not change, but the amount of the labeled antibody B that binds to the substance targeted for measurement A is relatively large. Therefore, the amount of the labeled antibody B bound to the text antigen D is relatively large. In this case, since the labeled antibody B that has been bound to the substance targeted for measurement A cannot bind to the mask antigen D, the amount of the labeled antibody B to be bound to the mask antigen D is relatively small. In addition to the labeled antibody B that is not bound to the substance targeted for measurement A, the labeled antibody B that is bound to the substance targeted for measurement A binds to the text antibody C, and the amount of the labeled antibody B to be bound to the mask antigen D is relatively small. As a result, since the color development of the portion of the mask antigen D in the judgement part 3 becomes weaker than of the portion of the text antibody C in the judgement part 3, the character(s) or figure(s) formed by the text antibody C become visible.

The competitive immunochromatographic sensor configured as described above may be housed in a suitable housing (not shown). Preferably, the housing is provided with a window portion that is arranged at the portion corresponding to the judgement part 3 so that the user can see the reaction result in the judgement part 3 through the window part.

According to the competitive immunochromatographic sensor of the present embodiment configured as described above, it is possible to semi-quantify the substance targeted for measurement in the test solution simply by dropping the test solution onto the test solution deposition section 1.

Figure 5:
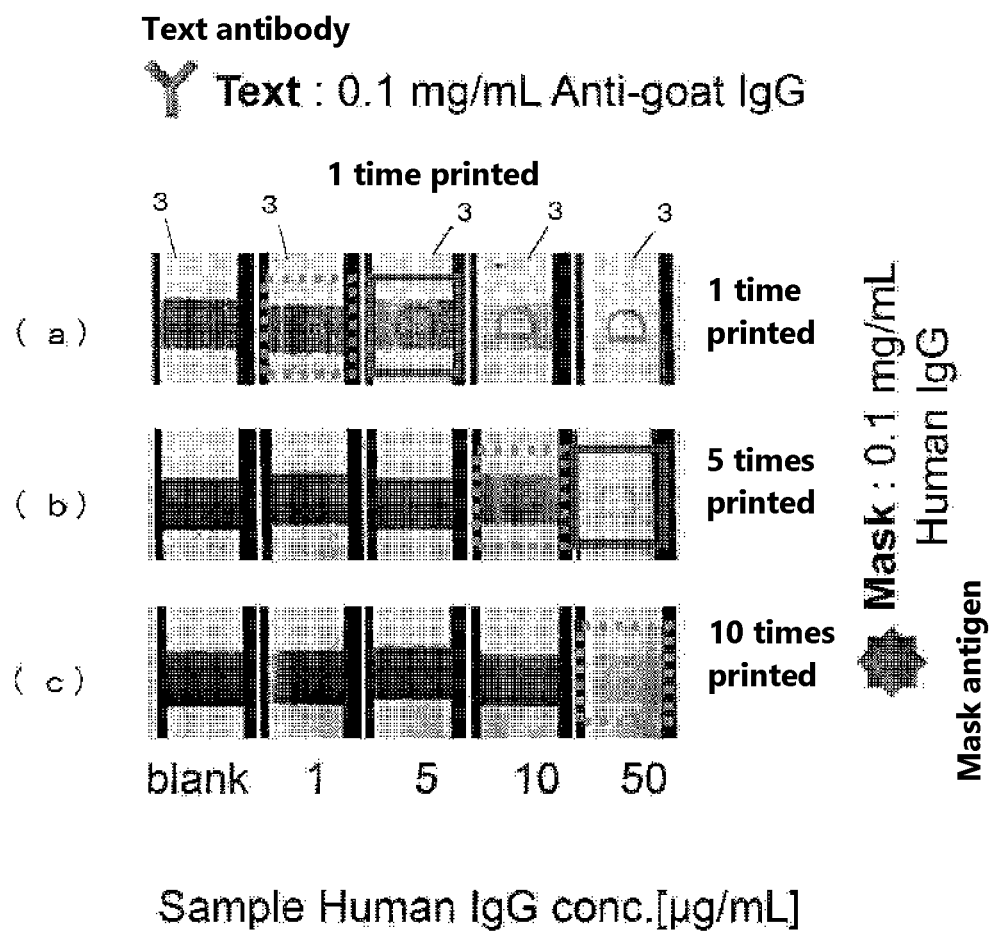
FIG. 5(a) shows results of measuring samples having different concentrations using five immunochromatographic sensors each having the judgement part in which the text antibody is printed once and the mask antigen is printed once.
FIG. 5(b) shows a results of measuring samples having different concentrations using five immunochromatographic sensors each having the judgement part in which the text antibody is printed once and the mask antigen is printed 5 times.
FIG. 5(c) shows results of measuring samples having different concentrations using five immunochromatographic sensors each having the judgement part in which the text antibody is printed once and the mask antigen is printed 10 times.
Figure 6:
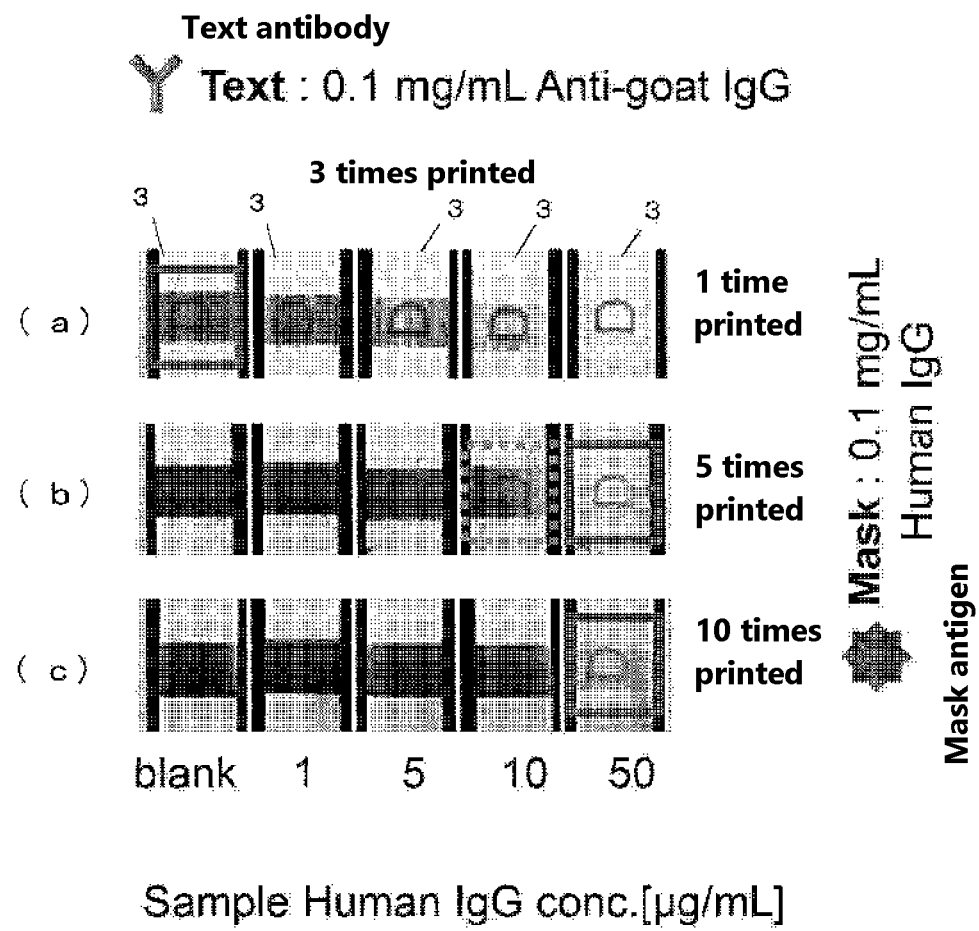
FIG. 6(a) shows results of measuring samples having different concentrations using five immunochromatographic sensors each having the judgement part in which the text antibody is printed 3 times and the mask antigen is printed once.
FIG. 6(b) shows results of measuring samples having different concentrations using five immunochromatographic sensors each having the judgement part in which the text antibody is printed 3 times and the mask antigen is printed 5 times.
FIG. 6(c) shows results of measuring samples having different concentrations using five immunochromatographic sensors each having the judgement part in which the text antibody is printed 3 times and the mask antigen is printed 10 times.
Figure 7:
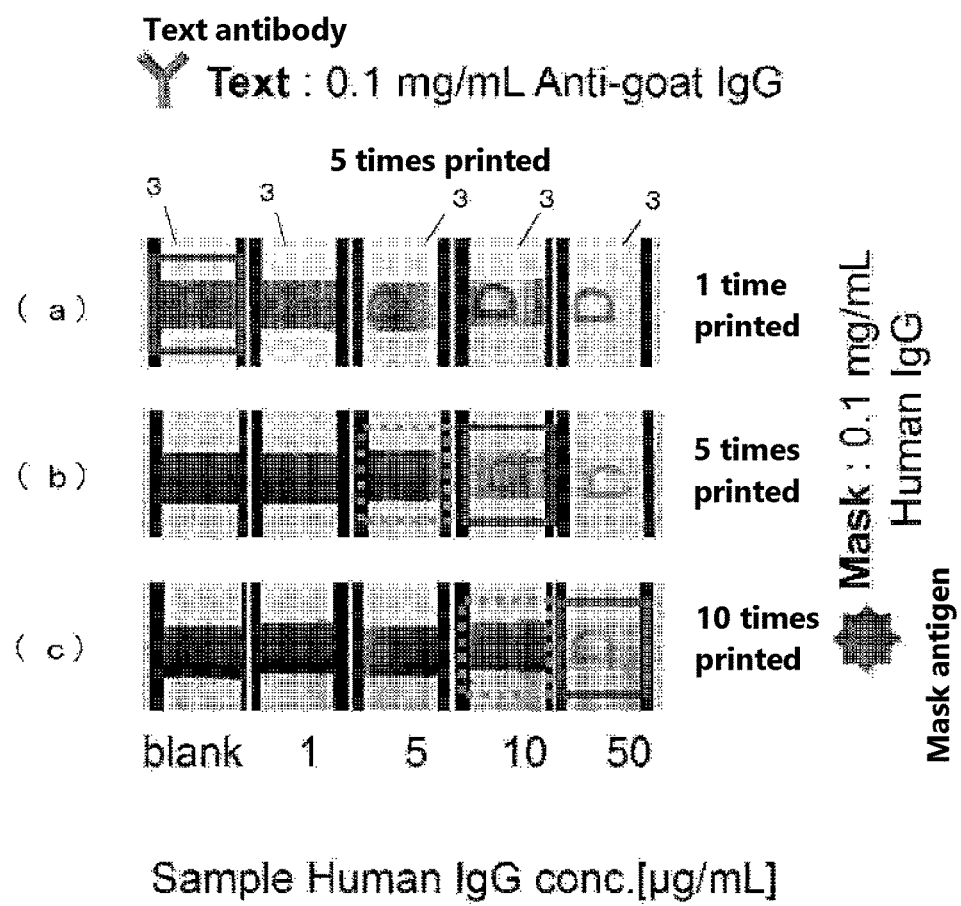
FIG. 7(a) shows results of measuring samples having different concentrations using five immunochromatographic sensors each having the judgement part in which the text antibody is printed 5 times and the mask antigen is printed once.
FIG. 7(b) shows results of measuring samples having different concentrations using five immunochromatographic sensors each having the judgement part in which the text antibody is printed 5 times and the mask antigen is printed 5 times.
FIG. 7(c) shows results of measuring samples having different concentrations using five immunochromatographic sensors each having the judgement part in which the text antibody is printed 5 times and the mask antigen is printed 10 times.

FIGS. 5 to 7 show results of actually measuring a substance targeted for measurement using the competitive immunochromatographic sensor configured as described above. These measurement results have been obtained by measuring five samples each having different concentration of the substance targeted for measurement using five of each of the nine types of sensors. Said nine types of sensors have a different amount of text antibody and mask antigen in the judgement part thereof.

In this embodiment, the text antibody C has been printed first, and then the mask antigen D has been printed so as to cover the text antibody C.

In this embodiment, anti-goat IgG has been used as the text antibody C, human IgG has been used as the mask antigen D, and anti-human IgG labeled with gold colloid has been used as the labeled antibody. And human IgG has been measured as sample solutions with 5 different concentrations (0 μg/mL, 1 μg/mL, 5 μg/mL, 10 μg/mL and 50 μg/mL).

Further, a conjugate pad used as the labeled antibody-containing portion 2 in each immunochromatographic sensor has been prepared by the following method.

1 mL of gold nanoparticle (753610, ALDRICH) has been put into a 1.5 mL tube, 100 μL of phosphate buffer PB (pH 7.4, 10 mM) containing 100 μg/mL anti-human IgG (I3382, SIGMA) has been added thereto, and the mixture has been allowed to stand for 15 minutes. Then 100 μL of phosphate buffer PB (pH 7.4, 10 mM) containing 10% (w/v) bovine serum albumin BSA (010-25783, Wako) and phosphate buffer PB containing 1% polyethylene glycol PEG20000 (pH 7.4, 10 mM) has been added to said mixture, and the mixture has been allowed to stand for 15 minutes. And said mixture has been centrifuged in a centrifuge (15000 rpm, 4° C., 30 min) to remove the supernatant, and then 50 μL of phosphate buffer PB (pH 7.4, 10 mM) containing 2% (w/v) bovine serum albumin BSA and 10% (w/v) sucrose has been added. Said mixture has been redissolved using an ultrasonic cleaner filled with ice water and then 5 μL of the redissolved mixture has been added per one conjugate pad (5×8 mn). Finally, the conjugate pads have been dried at 37° C. for 2 hours using a heat sterilizer.

FIG. 5(*a*) shows the state of the judgement part 3 of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensor is formed by printing the text antibody C once in the form of the letter "D" using an inkjet printer capable of printing the antibody having a concentration of 0.1 mg/mL, and printing mask antigen once using an inkjet printer capable of printing the antibody having a concentration of 0.1 mg/mL.

FIG. 5(*b*) shows the state of the judgement part 3 of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensor is formed by printing the text antibody C once in the form of the letter "D" using an inkjet printer capable of printing the antibody having a concentration of 0.1 mg/mL, and printing mask antigen D five times using an inkjet printer capable of printing the antigen having a concentration of 0.1 mg/mL.

FIG. 5(*c*) shows the state of the judgement part 3 of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensor is formed by printing the text antibody C once in the form of the letter "D" using the inkjet printer capable of printing the antibody having the concentration of 0.1 mg/mL, and printing mask antigen D ten times using the inkjet printer capable of printing the antigen having the concentration of 0.1 mg/mL.

FIG. 6(a) shows the state of the judgement part 3 of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensor is formed by printing the text antibody C three times in the form of the letter "D" using the inkjet printer capable of printing the antibody having the concentration of 0.1 mg/mL, and printing mask antigen D once using the inkjet printer capable of printing the antigen having a concentration of 0.1 mg/mL.

FIG. 6(b) shows the state of the judgement part 3 of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensor is formed by printing the text antibody C three times in the form of the letter "D" using the inkjet printer capable of printing the antibody having the concentration of 0.1 mg/mL, and printing mask antigen D five times using the inkjet printer capable of printing the antigen having the concentration of 0.1 mg/mL.

FIG. 6(c) shows the state of the judgement part 3 of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensor is formed by printing the text antibody C three times in the form of the letter "D" using the inkjet printer capable of printing the antibody having the concentration of 0.1 mg/mL, and printing mask antigen D ten times using the inkjet printer capable of printing the antigen having the concentration of 0.1 mg/mL.

FIG. 7(a) shows the state of the judgement part 3 of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensor is formed by printing the text antibody C five times in the form of the letter "D" using the inkjet printer capable of printing the antibody having the concentration of 0.1 mg/mL, and printing mask antigen D once using the inkjet printer capable of printing the antigen having the concentration of 0.1 mg/mL.

FIG. 7(b) shows the state of the judgement part 3 of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensor is formed by printing the text antibody C five times in the form of the letter "D" using the inkjet printer capable of printing the antibody having the concentration of 0.1 mg/mL, and printing mask antigen D five times using the inkjet printer capable of printing the antigen having the concentration of 0.1 mg/mL.

FIG. 7(c) shows the state of the judgement part 3 of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensor is formed by printing the text antibody C five times in the form of the letter "D" using the inkjet printer capable of printing the antibody having the concentration of 0.1 mg/mL, and printing mask antigen D ten times using the inkjet printer capable of printing the antigen having the concentration of 0.1 mg/mL.

From the results shown in FIGS. 5 to 7, it has been found that there is a correlation between the amounts of the text antibody and the mask antigen immobilized on the judgement part and the concentration of the substance targeted for measurement in the measurement sample. As a result, it has been confirmed that a cutoff value may be determined by the amount of the antibody and the mask antigen.

Then, a third embodiment in which a judgement part configured as described above is applied to an immunochromatographic sensor having a lateral flow structure will be described.

Figure 8:
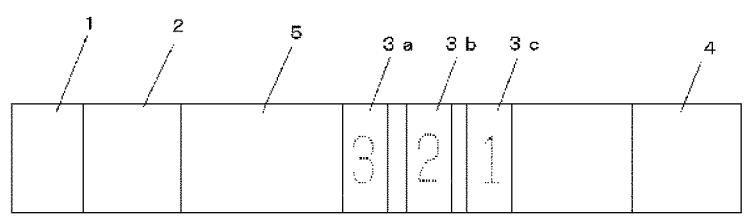
FIG. 8 is a schematic top view of a third embodiment of the immunochromatographic sensor according to the present invention.
Figure 9:
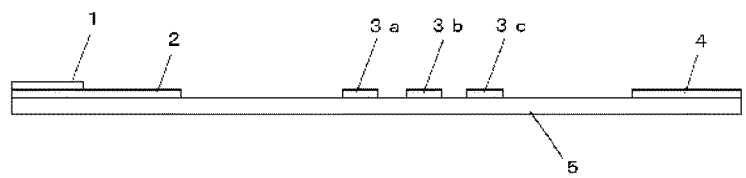
FIG. 9 is a schematic side view of the immunochromatographic sensor shown in FIG. 8.

FIG. 8 is a schematic top view of the third embodiment of the immunochromatographic sensor according to the present invention and FIG. 9 is a schematic side view of the immunochromatographic sensor shown in FIG. 8.

Since the configuration of the immunochromatographic sensor of this embodiment is the same as that of the immunochromatographic sensor of the second embodiment, except that three judgement parts 3a to 3c are provided in series, a duplicate description will be omitted in the following description.

Layouts of a text antibody C of the three judgement parts 3a to 3c are different from each other. In the judgement part 3a, the text antibody C is laid out in the form of numeral "3", in the judgement part 3b, the text antibody C is laid out in the form of numeral "2", and in the judgement part 3c, the text antibody C is laid out in the form of numeral "1".

In addition, the amounts of a mask antigen D of the three judgement parts 3a to 3c are different from each other. In the judgement part 3a, the mask antigen D is printed, for example, 10 times, in the judgement part 3b, the mask antigen D is printed, for example, 5 times, and in the judgement part 3c, the mask antigen D is printed, for example, once. On the other hand, the text antibody C of the three judgement parts 3a to 3c have different forms but the same amount. As a result, the amount of mask antigen D related to the text antibody C decreases as it goes downstream. Therefore, the appearances of the numeral with respect to the content of the substance to be measured A in the test solution differ between the three judgement parts 3a to 3c.

That is, according to the above configuration, the content of the substance to be measured A by which the numeral can appear in the judgement part 3b is less than that by which the numeral can appear in the judgement part 3a. And the content of the substance to be measured A by which the numeral can appear in the judgement part 3c is less than that by which the numeral can appear in the judgement part 3b. In this way, the content of the substance to be measured A at which the numeral can be appear in each judgement part 3a to 3c can be adjusted with the amounts of the text antibody C and the mask antigen D, so that the content of the substance to be measured A may be semi-quantified.

In the above-mentioned embodiment, the ratio of the amount of mask antigen D to the text antibody C in the downstream judgement part is lower than the ratio of that in the upstream judgement part, however it is possible that the ratio of the amount of mask antigen D to the text antibody C in the downstream judgement part is higher than the ratio of that in the upstream judgement part without limiting to this embodiment.

Even with said configuration, the content of the substance to be measured A at which the numeral can appear in the three judgement parts 3a to 3c may be changed, and therefore, by adjusting the amounts of the text antibody C and the mask antigen D, the content of the measurement substance A may be semi-quantified.

FIGS. 10 to 13 show results of measuring samples having different concentrations using five immunochromatographic sensors each having three judgement parts with different amounts of the text antibody C and the mask antigen D. In addition, in the embodiments of FIGS. 10, 11, 12 and 13, the ratios of the amount of the text antibody C and the mask antigen D are different from each other.

In these embodiments, anti-goat IgG is used as the text antibody C, human IgG is used as the mask antigen D, and anti-human IgG labeled with gold colloid is used as the labeled antibody. In each embodiment, tests have been carried out using a plurality of test solutions with different concentrations of human IgG.

In these embodiments, at first the text antibody C is printed and then the mask antigen D is printed so as to cover the text antibody C.

The conjugate pad constituting the labeled antibody containing section 2 is the same as the one of the embodiments shown in FIGS. 5 to 7.

The amount of the text antibody C and the amount of the mask antigen D to be immobilized on the judgement part 3 are adjusted by changing the number of cycles of the inkjet printing.

The text antibodies C are printed in the form of "1", "2", and "3" using the inkjet printer capable of printing antibody having the concentration of 0.1 mg/mL.

The mask antigens D are printed using the inkjet printer capable of printing antigen having the concentration of 0.1 mg/mL.

Five samples have been used, and the concentrations of human IgG as a substance to be measured A in each sample are 0 μg/mL, 1 μg/mL, 5 μg/mL, 10 μg/mL, and 50 μg/mL.

Figure 10:
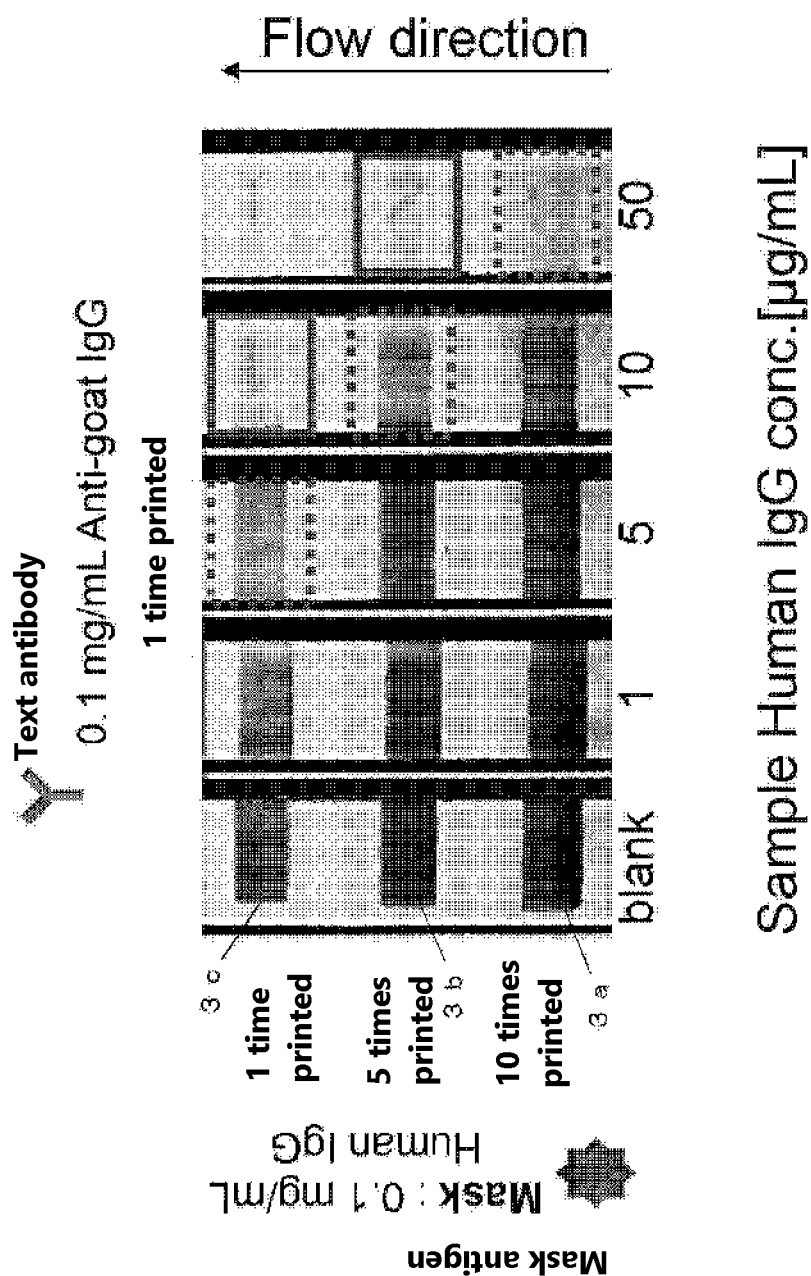
FIG. 10 shows results of measuring samples having different concentrations using five immunochromatographic sensors each having three judgement parts each having different amounts of the text antibody and the mask antigen.

FIG. 10 shows states of the judgement parts 3a to 3c of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensors is formed by the following method. That is, the text antibody is printed once on all the judgement parts 3a to 3c, mask antigen D is printed 10 times on the most upstream judgement part 3a, the mask antigen D is printed 5 times on the next judgement part 3b, and the mask antigen D is printed once on the most downstream judgement part 3c.

Figure 11:
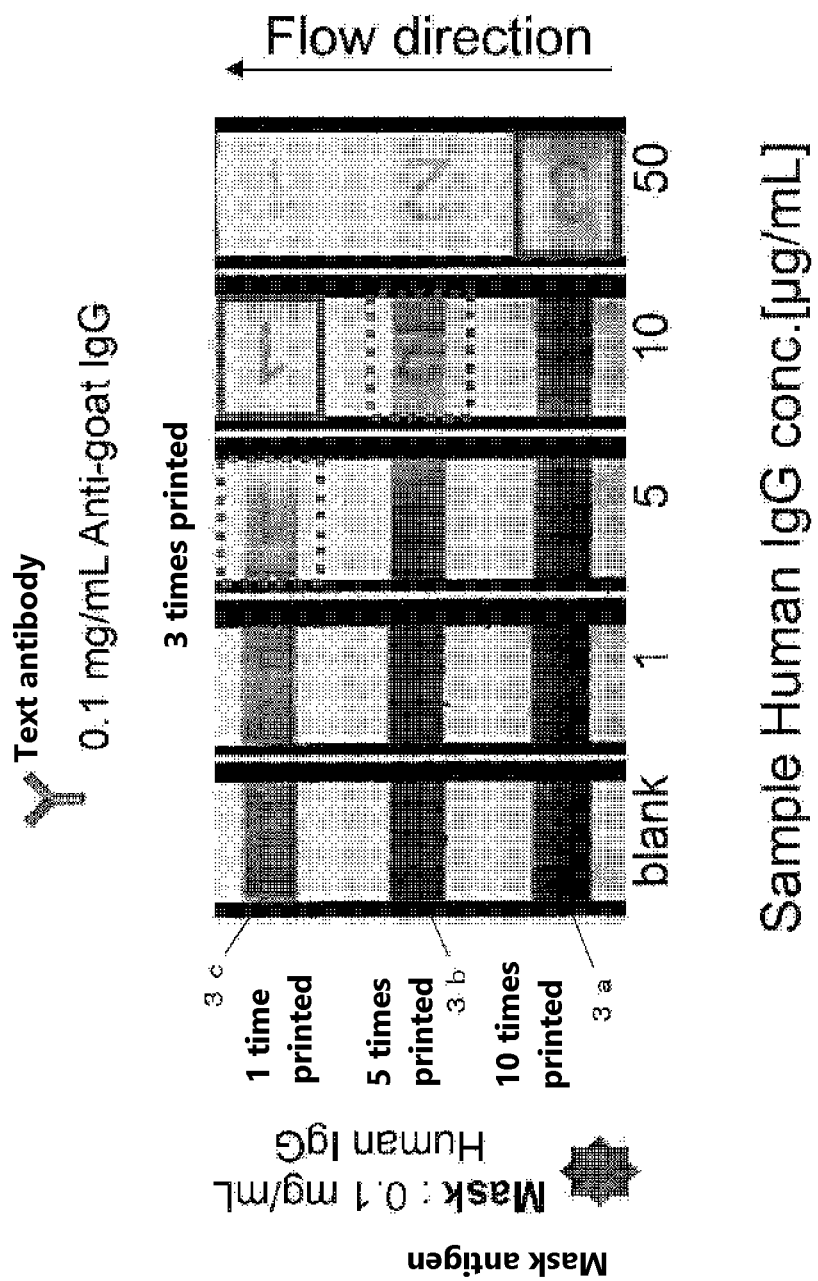
FIG. 11 shows results of measuring samples having different concentrations using five immunochromatographic sensors each having three judgement parts each having different amounts of the text antibody and the mask antigen.

FIG. 11 shows states of the judgement parts 3a to 3c of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensors is formed by the following method. That is, the text antibody is printed 3 times on all the judgement parts 3a to 3c, mask antigen D is printed 10 times on the most upstream judgement part 3a, the mask antigen D is printed 5 times on the next judgement part 3b, and the mask antigen D is printed once on the most downstream judgement part 3c.

Figure 12:
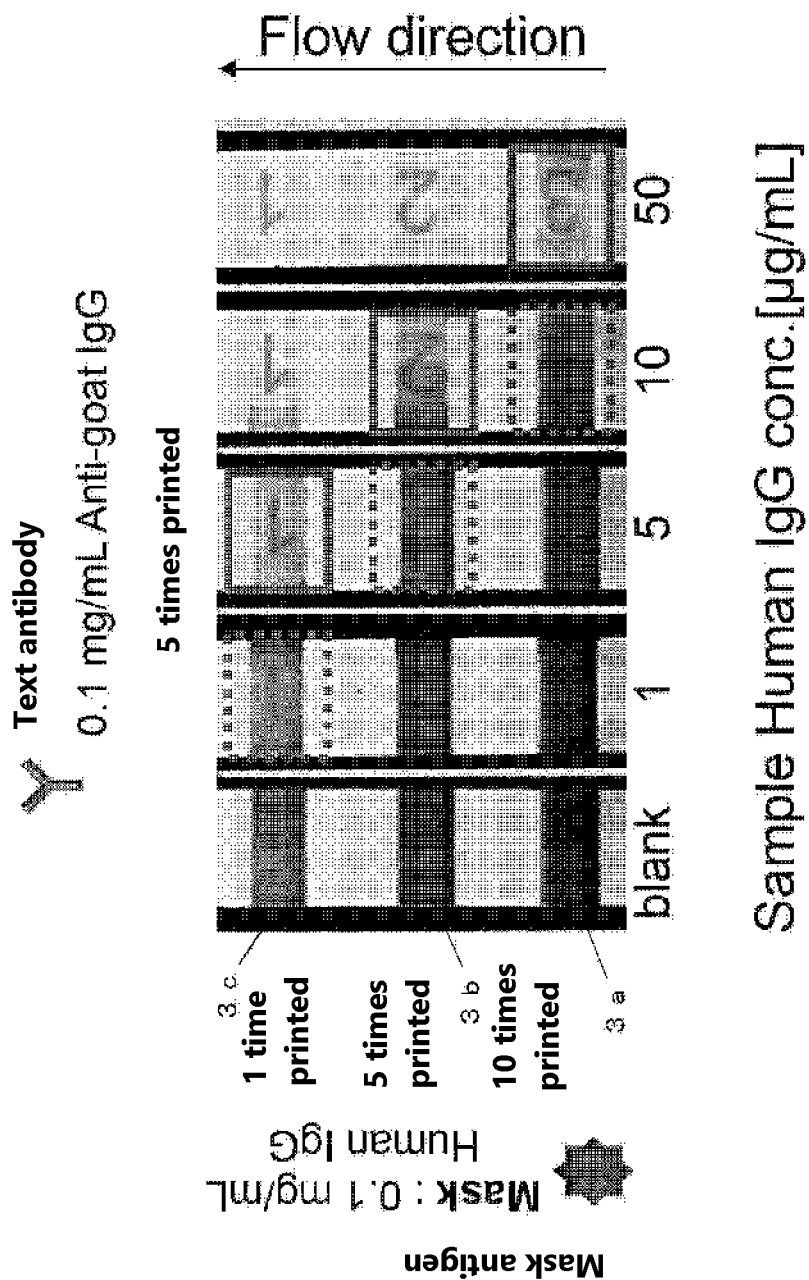
FIG. 12 shows results of measuring samples having different concentrations using five immunochromatographic sensors each having three judgement parts each having different amounts of the text antibody and the mask antigen.

FIG. 12 shows states of the judgement parts 3a to 3c of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensors is formed by the following method. That is, the text antibody is printed 5 times on all the judgement parts 3a to 3c, mask antigen D is printed 10 times on the most upstream judgement part 3a, the mask antigen D is printed 5 times on the next judgement part 3b, and the mask antigen D is printed once on the most downstream judgement part 3c.

Figure 13:
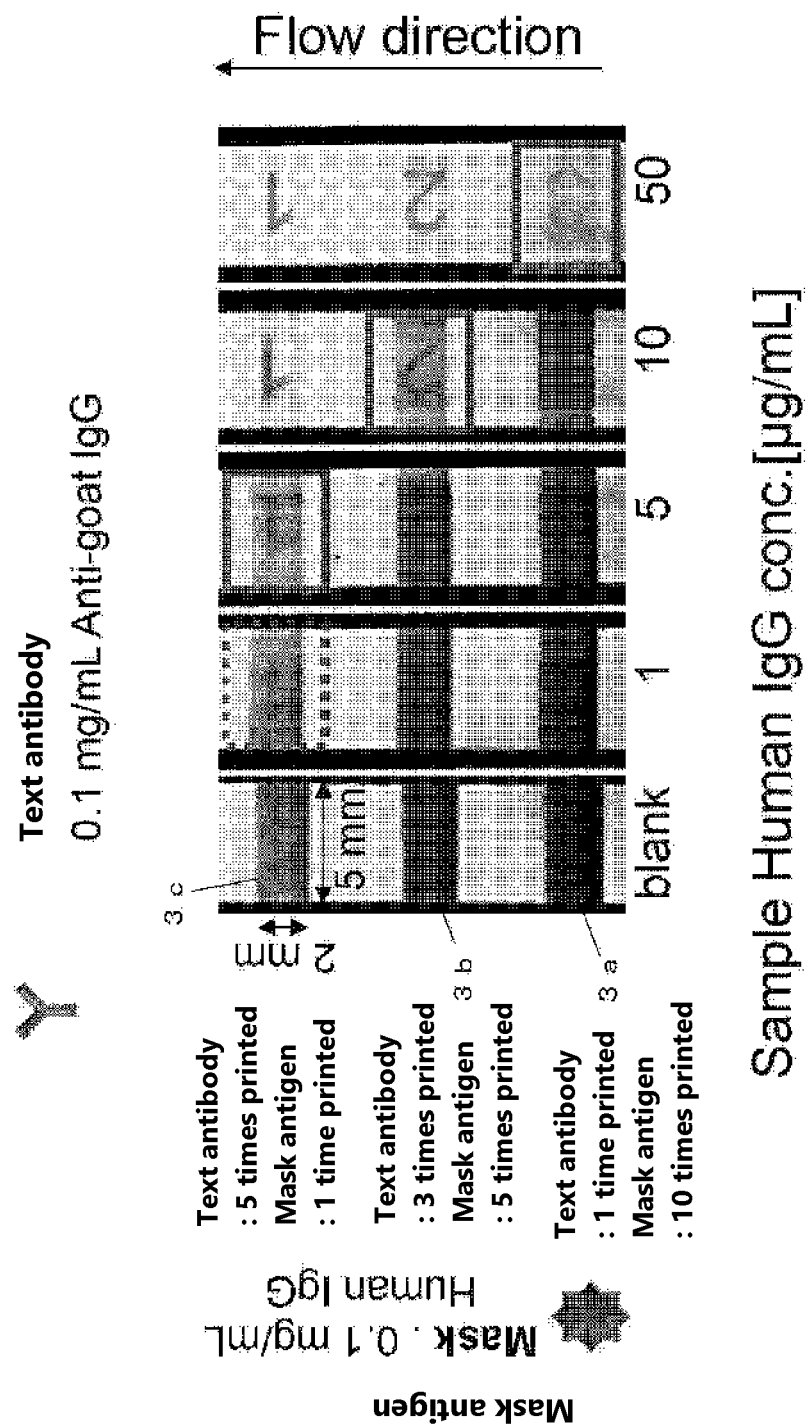
FIG. 13 shows results of measuring samples having different concentrations using five immunochromatographic sensors each having three judgement parts each having different amounts of the text antibody and the mask antigen.

FIG. 13 shows states of the judgement parts 3a to 3c of each immunochromatographic sensor when five sample solutions having different concentrations (0 μg/mL, 1 μg/mL, 5 μg/mL, 10 μg/mL and 50 μg/mL) have been measured using five immunochromatographic sensors. Each judgement part of said immunochromatographic sensors is formed by the following method. That is, the text antibody is printed once and then the mask antigen D is printed 10 times on the judgement part 3a, the text antibody is printed 3 times and then the mask antigen D is printed 5 times on the judgement part 3b, and the text antibody is printed 5 times and then the mask antigen D is printed once on the judgement part 3c.

As shown in FIGS. 10 to 13, it has been confirmed that by adjusting the amounts of the text antibody and the mask antigen, it is possible to identify and judge the test solutions having different concentrations of the substance to be measured A. As a result, it has been confirmed that by adjusting the amounts of the text antibody and the mask antigen, the concentration of the substance to be measured A can be semi-quantified.

In the above-mentioned embodiments, human IgG is used as the substance to be measured, but the measurement substance is not limited to the above embodiments, and any substance may be used, for example, 8-OHdG can be used as the substance to be measured. In case that 8-OHdG is the substance to be measured, anti-8-OHdG (derived from rat) may be used as the labeled antibody and for example anti-rat IgG may be used as the text antibody. And 8-OHdG/BSA conjugate is used as the mask antigen. Further, when forming the judgement part for measuring 8-OHdG the mask antigen may be printed first, and then the text antibody may be printed on the mask antigen.

Then, a fourth embodiment in which the judgement part configured to measure 8-OHdG is applied to a competitive immunochromatographic sensor having a lateral flow structure will be described below.

FIG. 14 is a schematic top view of the fourth embodiment of the immunochromatographic sensor according to the present invention. FIG. 15 is a schematic side view of the immunochromatographic sensor shown in FIG. 14. FIG. 16 shows the amounts of the text antibody C and the mask antigen D in each judgement part by the number of printings.

Since the configuration of the immunochromatographic sensor of this embodiment is the same as that of the third embodiment except that a confirmation part 6 is provided downstream of the judgement parts 3a to 3c arranged in series, a duplicate description will be omitted in the following description.

In this embodiment, the mask antigen D is printed first, and then the text antibody C is printed on the mask antigen D.

In this embodiment, anti-rat IgG is used as the text antibody C, 8-OHdG/BSA conjugate is used as the mask antigen D, and anti-8-OHdG labeled with gold colloid is used as the labeled antibody. And 8-OHdG has been measured in sample solutions with 4 different concentrations (0 ng/mL, 5 ng/mL, 10 ng/mL and 25 ng/mL).

Further, a conjugate pad used as the labeled antibody-containing portion 2 in each immunochromatographic sensor is prepared by the following method.

1 mL of gold nanoparticles (753610, Sigma-Aldrich) has been put into a 2 mL tube, 100 μL of 40 μL anti-8-OHdG has been added thereto, and the mixture has been shaken for 30 minutes. Then, 100 μL of 10% (w/v) bovine serum albumin BSA (010-25783, Wako) and 50 μL of 1% (w/v) polyethylene glycol PEG20000 (168-11285, Wako) has been added to said mixture, and then the mixture has been shaken for 10 minutes. And then, 450 μL of storage buffer for a conjugate pad (tris-hydrochloric acid buffer (pH 8.2, 20 mM) containing 0.05% (w/v) polyethylene glycol PEG20000, 1% (w/v) BSA, 0.1% (w/v) sodium azide, and 150 mM sodium chloride) has been added thereto. Then, said mixture has been centrifuged in a centrifuge (2500 g, 4° C., 30 min) to remove the supernatant, and then 75 μL of coating buffer for the conjugate pad (tris-hydrochloric acid buffer (pH 8.2, 20 mM) containing 0.05% (w/v) polyethylene glycol PEG20000, 5% (w/v) sucrose, and 150 mM sodium chloride) and 33 μL ultrapure water have been added thereto. Said mixture has been re-dissolved using a vortex mixer and then 25 μL of the re-dissolved mixture has been added per one conjugate pad (5×8 mn) and then has been dried at 37° C. for 2 hours using a heat sterilizer.

The Layouts of the text antibody C of the three judgement parts 3a to 3c and the confirmation part 6 are different from each other. In the judgement part 3a, the text antibody C is laid out in the form of character "Lo", in the judgement part 3b, the text antibody C is laid out in the form of character "Md", and in the judgement part 3c, the text antibody C is laid out in the form of character "Hi". In the confirmation part 6, the text antibody C is laid out in the form of character "Tr".

In addition, the amounts of the text antibody C of the three judgement parts 3a to 3c and the confirmation part 6 are different from each other. In the judgement part 3a, the text antibody C is printed, for example, 14 times, in the judgement part 3b, the text antibody C is printed, for example, 10 times, in the judgement part 3c, the text antibody C is printed, for example, 6 times, and in the confirmation part 6, text antibody C is printed, for example, 20 times.

Further, the amounts of the mask antigen D of the three judgement parts 3a to 3c are different from each other. In the judgement part 3a, the mask antigen D is printed, for example, 10 times, in the judgement part 3b, the mask antigen D is printed, for example, 15 times, and in the judgement part 3c, the mask antigen D is printed, for example, 20 times.

As a result, the amount of the text antigen C related to the mask antigen D decreases as it goes downstream. Therefore, the appearances of the characters with respect to the content of the substance to be measured A in the test solution are changed between the three judgement parts 3a to 3c.

That is, according to the above configuration, the content of the substance to be measured A at which the character can appear in the judgement part 3b is less than that at which the character can appear in the judgement part 3c. And the content of the substance to be measured A at which the character can appear in the judgement part 3a is less than that at which the character can appear in the judgement part 3b. On the other hand, in the confirmation part 6, the character can appear regardless of the content of the substance to be measured A. In this way, by adjusting the amount of the text antibody C and the mask antigen D on the judgement parts 3a to 3c, the content of the substance to be measured A may be semi-quantified.

Figure 17:
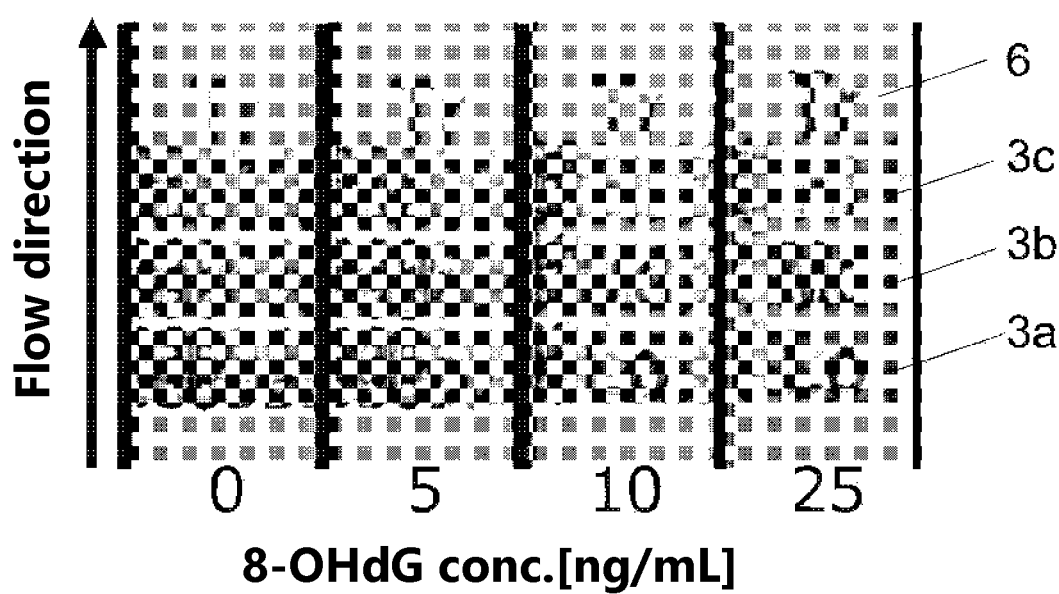
FIG. 17 shows results of measuring samples having different concentrations using immunochromatographic sensors each having a confirmation part and three judgement parts each having different amounts of the text antibody and the mask antigen.

FIG. 17 shows results of measuring samples having different concentrations using four immunochromatographic sensors each having three judgement parts with different amounts of the text antibody C and the mask antigen D and one confirmation part 6. Since the basic configuration of the immunochromatographic sensor of this embodiment is the same as that described with reference to FIGS. 14 to 16, only the portions corresponding to the three judgement parts 3a to 3c and the confirmation part 6 are shown in FIG. 17.

In this embodiment, anti-rat IgG is used as the text antibody C, 8-OHdG/BSA conjugate is used as the mask antigen D, and anti-8-OHdG labeled with gold colloid is used as the labeled antibody. In this embodiment, tests have been carried out using a plurality of test solution with different concentrations of 8-OHdG.

In this embodiment, the mask antigen D is printed first, and then the text antibody is printed on the mask antigen D.

The conjugate pad constituting the labeled antibody containing section 2 is the same as the one of the embodiments shown in FIGS. 14 to 16.

The amounts of the text antibody C and the mask antigen D to be immobilized on the judgement part 3 are adjusted by changing the number of cycles of the inkjet printing.

The text antibodies C are printed in the form of "Tr", "Hi", "Md" and "Lo" using the inkjet printer capable of printing antibody having the concentration of 0.1 mg/mL.

The mask antigens D are printed using the inkjet printer capable of printing antigen having a concentration of 0.1 mg/mL.

Four samples have been used, and the concentrations of 8-OHdG as a substance to be measured in each sample are 0 ng/mL, 5 ng/mL, 10 ng/mL, and 25 ng/mL.

FIG. 17 shows states of the judgement parts 3a to 3c and the confirmation part 6 of each immunochromatographic sensor when four sample solutions having different concentrations (0 ng/mL, 5 ng/mL, 10 ng/mL and 25 ng/mL) have been measured using four immunochromatographic sensors. Each judgement part and the confirmation part of said immunochromatographic sensor is formed by the following method. That is, the text antibody is printed 14 times and mask antigen D is printed 10 times on the judgement part 3a, the text antibody is printed 10 times and mask antigen D is printed 15 times on the judgement part 3b, and the text antibody is printed 6 times and mask antigen D is printed 20 times on the judgement part 3c. And for the confirmation part 6, text antibody is printed 20 times.

As shown in FIG. 17, it has been confirmed that by adjusting the amounts of the text antibody and the mask antigen, it is possible to identify and judge the test solutions having different concentrations of 8-OHdG as the substance to be measured A. As a result, it has been confirmed that by adjusting the amounts of the text antibody and the mask antigen, the concentration of 8-OHdG as the substance to be measured A can be semi-quantified.

DESCRIPTION OF REFERENCE NUMERALS

A substance targeted for measurement
B labeled antibody
C text antibody
D mask antigen
1 test solution deposition section
2 labeled antibody containing section
3 judgement part
4 test solution absorption part
5 membrane carrier
6 confirmation part

What is claimed is:

1. Competitive immunochromatographic analysis method characterized in that the method comprises:
supplying a mixed solution in which a test solution containing a substance to be measured A and a labeled antibody B are mixed to one or more judgement parts, wherein said judgement parts are formed by immobilizing a text antibody C which specifically reacts with the labeled antibody B specifically reacting with the substance to be measured A on a membrane carrier in the form of character(s) or figure(s) and immobilizing a mask antigen D that is the same antigen as the substance to be measured A on the membrane carrier so as to surround said text antibody C, competitively binding the mixed solution having the labeled antibody B and the substance to be measured A to the mask antigen D and the text antibody C on the judgement parts, and judging the concentration of the substance to be measured A based on the signal from the labeled antibody B bound to the text antibody C and the mask antigen D.

2. The analysis method according to claim 1, characterized in that a plurality of judgement parts is provided on the membrane carrier, and the ratios of the amounts of the text antibody C and the mask antigen D in each judgment part of said plurality of judgement parts are different from each other.

3. The analysis method according to claim 2, characterized in that the plurality of judgement parts is provided on the membrane carrier along a flow direction of the test solution, and the ratio of the amount of mask antigen D related to the text antibody C on the judgement part placed downstream is lower than the ratio of the amount of mask antigen D related to the text antibody C on the other judgement parts placed upstream.

4. The analysis method according to claim 2, characterized in that a plurality of judgement parts is provided on the membrane carrier along a flow direction of the test solution, the ratio of the amount of mask antigen D related to the text antibody C on the judgement part placed downstream is higher than the ratio of the amount of mask antigen D related to the text antibody C on the other judgement parts placed upstream.

5. The analysis method according to claim 1, characterized in that the text antibody C and the mask antigen D are inkjet printed on the membrane carrier.

6. The analysis method according to claim 2, characterized in that the text antibody C and the mask antigen D are inkjet printed on the membrane carrier.

7. The analysis method according to claim 3, characterized in that the text antibody C and the mask antigen D are inkjet printed on the membrane carrier.

8. The analysis method according to claim 4, characterized in that the text antibody C and the mask antigen D are inkjet printed on the membrane carrier.

* * * * *